United States Patent
Yanagihara et al.

(10) Patent No.: US 10,582,976 B2
(45) Date of Patent: Mar. 10, 2020

(54) MANIPULATOR SYSTEM AND MANIPULATOR CONTROL METHOD

(71) Applicant: OLYMPUS CORPORATION, Tokyo (JP)

(72) Inventors: Masaru Yanagihara, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/055,394

(22) Filed: Aug. 6, 2018

(65) Prior Publication Data

US 2018/0338809 A1    Nov. 29, 2018

Related U.S. Application Data

(63) Continuation of application No. PCT/JP2016/053937, filed on Feb. 10, 2016.

(51) Int. Cl.
| | | |
|---|---|---|
| *G06F 19/00* | (2018.01) | |
| *A61B 34/30* | (2016.01) | |
| *A61B 90/00* | (2016.01) | |
| *A61B 34/20* | (2016.01) | |

(52) U.S. Cl.
CPC ...... *A61B 34/30* (2016.02); *A61B 2034/2059* (2016.02); *A61B 2034/2061* (2016.02); *A61B 2034/301* (2016.02); *A61B 2090/061* (2016.02); *A61B 2090/067* (2016.02)

(58) Field of Classification Search
CPC .................. A61B 90/00; B25J 18/06
See application file for complete search history.

(56) References Cited

U.S. PATENT DOCUMENTS

| | | | | |
|---|---|---|---|---|
| 5,897,488 A | * | 4/1999 | Ueda ........................ | B25J 18/06 600/143 |
| 9,999,477 B2 | * | 6/2018 | Takahashi ............ | A61B 1/0052 |
| 2009/0143642 A1 | * | 6/2009 | Takahashi .......... | A61B 1/00147 600/106 |

(Continued)

FOREIGN PATENT DOCUMENTS

| | | |
|---|---|---|
| EP | 2064984 A2 | 6/2009 |
| EP | 2213221 A1 | 8/2010 |

(Continued)

OTHER PUBLICATIONS

International Search Report dated May 10, 2016 issued in PCT/JP2016/053937.

(Continued)

*Primary Examiner* — Harry Y Oh
(74) *Attorney, Agent, or Firm* — Scully, Scott, Murphy & Presser, P.C.

(57) ABSTRACT

Provided is a manipulator system including: a driver provided at a proximal end of a flexible elongated guide member to drive a distal end of the elongated guide member, a slider that is fixed to the proximal end of the elongated guide member and that is movable with respect to the driver in a longitudinal direction of the elongated guide member, and a controller that is configured to control the driver so as to change a moving amount of the slider in accordance with a bending state of the elongated guide member.

7 Claims, 15 Drawing Sheets

(56) References Cited

U.S. PATENT DOCUMENTS

| | | | | |
|---|---|---|---|---|
| 2011/0071564 A1* | 3/2011 | Suzuki | ............ | A61B 17/29 606/205 |
| 2011/0106141 A1* | 5/2011 | Nakamura | ............ | A61B 34/71 606/205 |
| 2012/0046522 A1* | 2/2012 | Naito | ............ | A61B 1/00006 600/118 |
| 2016/0001447 A1 | 1/2016 | Iida | | |
| 2016/0135908 A1 | 5/2016 | Takahashi et al. | | |
| 2017/0209227 A1* | 7/2017 | Yoshimura | ............ | B25J 1/02 |
| 2017/0325904 A1* | 11/2017 | Hyodo | ............ | A61B 34/73 |
| 2018/0214226 A1* | 8/2018 | Kan | ............ | B25J 17/02 |

FOREIGN PATENT DOCUMENTS

| | | |
|---|---|---|
| EP | 2305144 A1 | 4/2011 |
| EP | 2409657 A1 | 1/2012 |
| EP | 2517613 A1 | 10/2012 |
| EP | 3 025 630 A1 | 6/2016 |
| JP | 2009-131374 A | 6/2009 |
| JP | 4601727 B2 | 12/2010 |
| JP | 5048158 B2 | 10/2012 |
| JP | 2014-023721 A | 2/2014 |
| JP | 5550150 B2 | 7/2014 |
| JP | 2015-024032 A | 2/2015 |
| WO | WO 2010/106714 A1 | 9/2010 |
| WO | 2014/098246 A1 | 6/2014 |
| WO | 2015/012179 A1 | 1/2015 |

OTHER PUBLICATIONS

JP Decision to Grant a Patent dated Jun. 20, 2017 issued in JP 2017-524482.
Extended Supplementary European Search Report dated Aug. 21, 2019 in European Patent Application No. 16 88 9807.0.

* cited by examiner

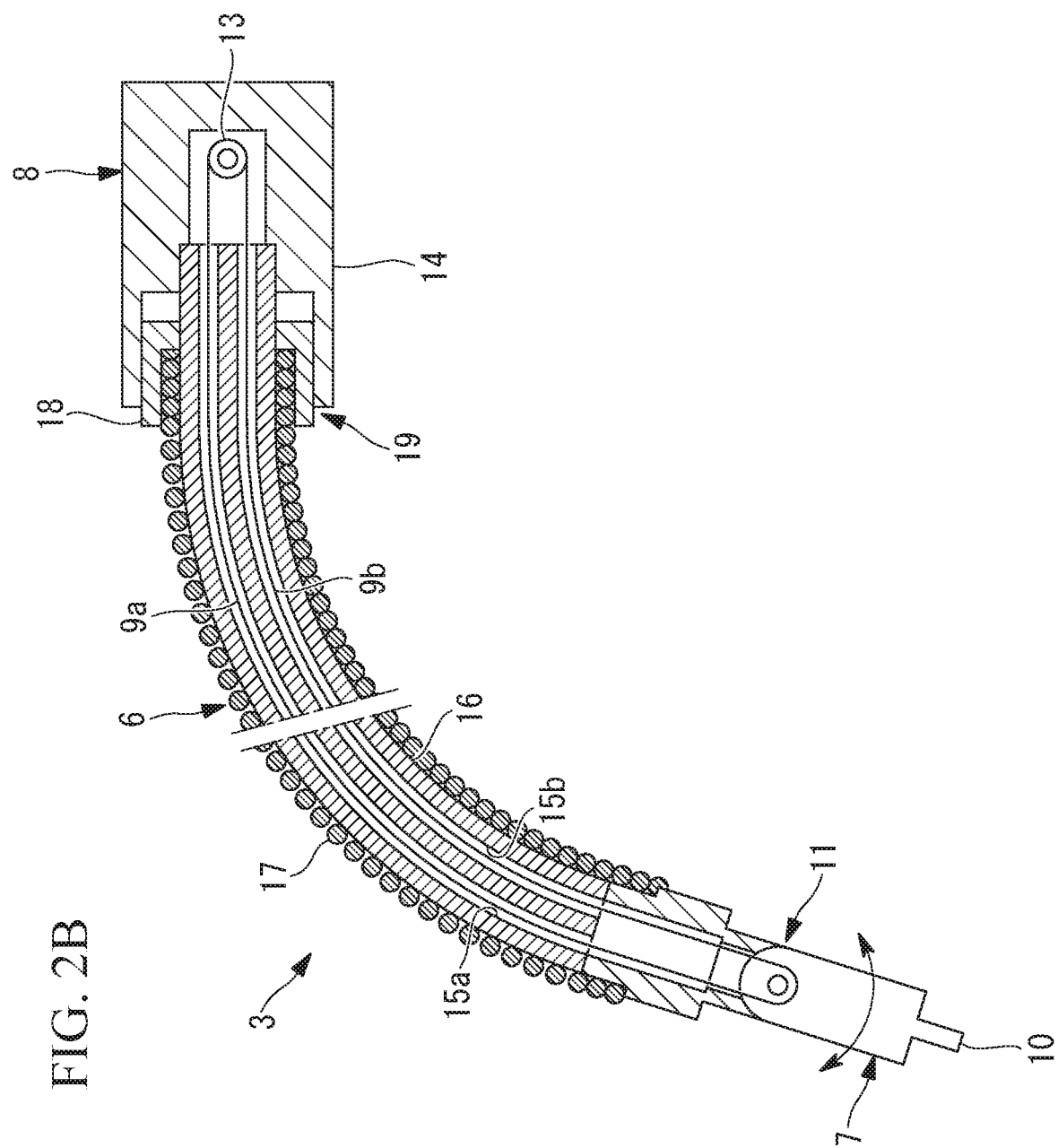

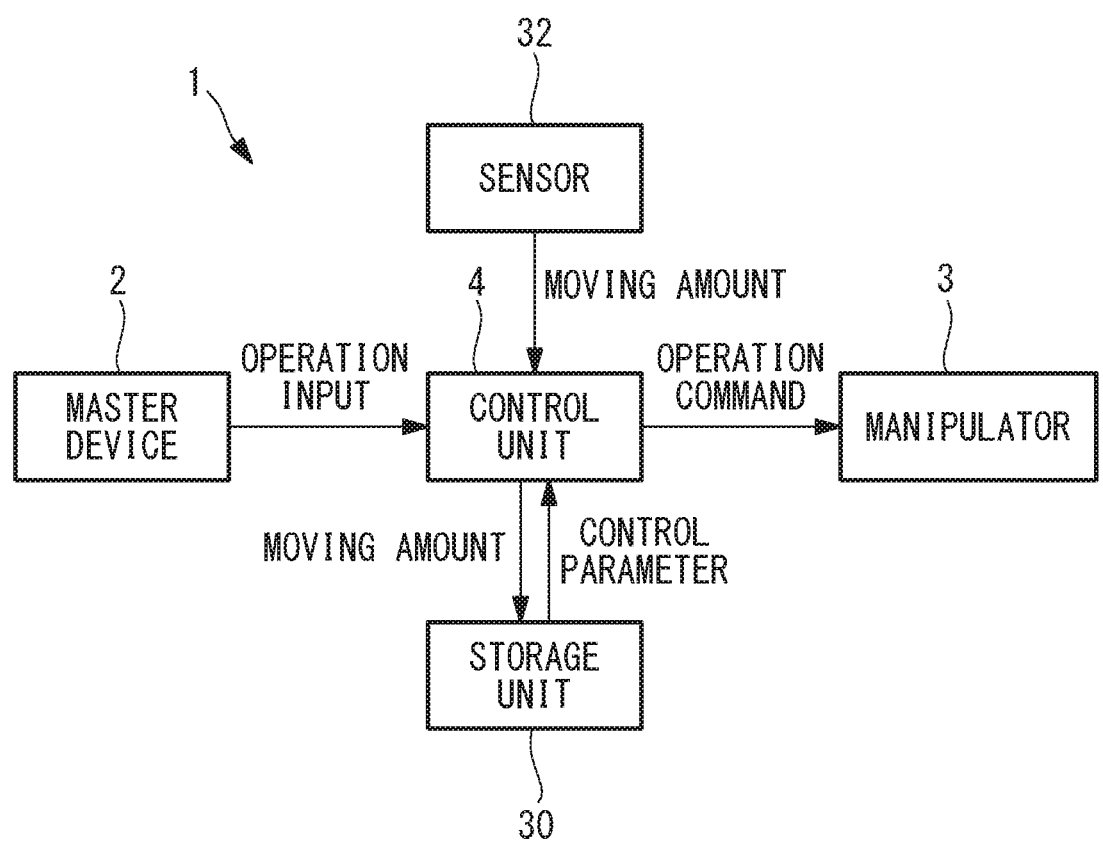
FIG. 8 (AMENDED)

MANIPULATOR SYSTEM AND MANIPULATOR CONTROL METHOD

CROSS-REFERENCE TO RELATED APPLICATIONS

This is a continuation of International Application PCT/JP2016/53937, with an international filing date of Feb. 10, 2016, which is hereby incorporated by reference herein in its entirety.

TECHNICAL FIELD

The present invention relates to a manipulator system and a control method thereof.

BACKGROUND ART

There is a known endoscope, catheter, or manipulator having a system in which a bending portion or a movable portion, such as forceps, disposed at the distal end of an insertion portion is driven by means of a wire (for example, see Patent Literatures 1 and 2).

In these Patent Literatures 1 and 2, a long, flexible insertion portion, in which the outer circumference of a flexible multilumen tube is covered with a coil tube, is employed, a wire is guided so as to penetrate through a lumen formed in the multilumen tube, and the coil tube enables torque transmission.

CITATION LIST

Patent Literature

{PTL 1} Japanese Unexamined Patent Application, Publication No. 2014-23721
{PTL 2} Publication of Japanese Patent No. 5550150, Specification

SUMMARY OF INVENTION

One aspect of the present invention is directed to a manipulator system including: a driver provided at a proximal end of a flexible elongated guide member to drive a distal end of the elongated guide member, a slider that is fixed to the proximal end of the elongated guide member and that is movable with respect to the driver in a longitudinal direction of the elongated guide member, and a controller that is configured to control the driver so as to change a moving amount of the slider in accordance with a bending state of the elongated guide member.

Another aspect of the present invention is directed to a manipulator system including: a manipulator; an operation unit for performing an input for operating the manipulator; a controller that is configured to control the manipulator on a basis of the input to the operation unit; a driver that is provided at a proximal end of the manipulator and that drives a movable portion provided at a distal end of the manipulator; a flexible elongated guide member that causes the movable portion to bend with respect to the driver by using a power transmission member that transmits motive power of the driver to the movable portion; and a slider that is fixed to a proximal end of the elongated guide member and that is movable with respect to the driver in a longitudinal direction of the elongated guide member, wherein the controller is configured to control the driver to change a moving amount of the slider in accordance with a bending state of the elongated guide member.

Another aspect of the present invention is directed to a manipulator control method including: detecting, by a sensor, an amount by which a slider, which is connected to a proximal end of a flexible elongated guide member, moves by causing a distal end of the elongated guide member to bend with respect to the proximal end of the elongated guide member; and controlling, by a controller, the driver so as to change a moving amount of the slider on a basis of a result of detection by the sensor.

BRIEF DESCRIPTION OF DRAWINGS

FIG. 2B is a longitudinal cross-sectional view showing a state in which the elongated guide member of the manipulator provided in the manipulator system in FIG. 1 is bent.

FIG. 8 is a block diagram showing a modification of the manipulator system in FIG. 1.

DESCRIPTION OF EMBODIMENT

A manipulator system 1 according to an embodiment of the present invention will be described below with reference to the drawings.

Figure 1:
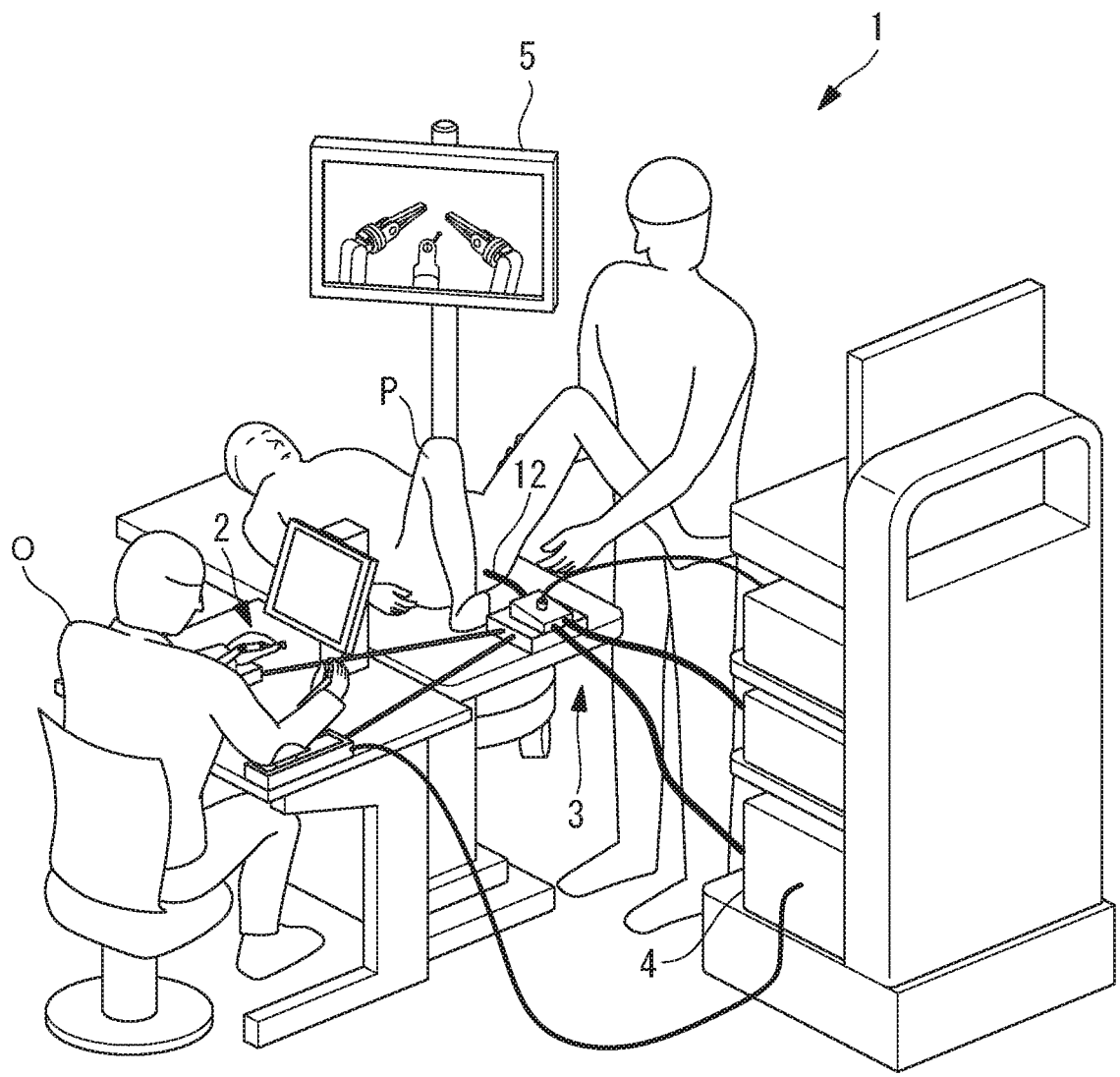
FIG. 1 is an overall configuration diagram showing a manipulator system according to an embodiment of the present invention.
Figure 4:
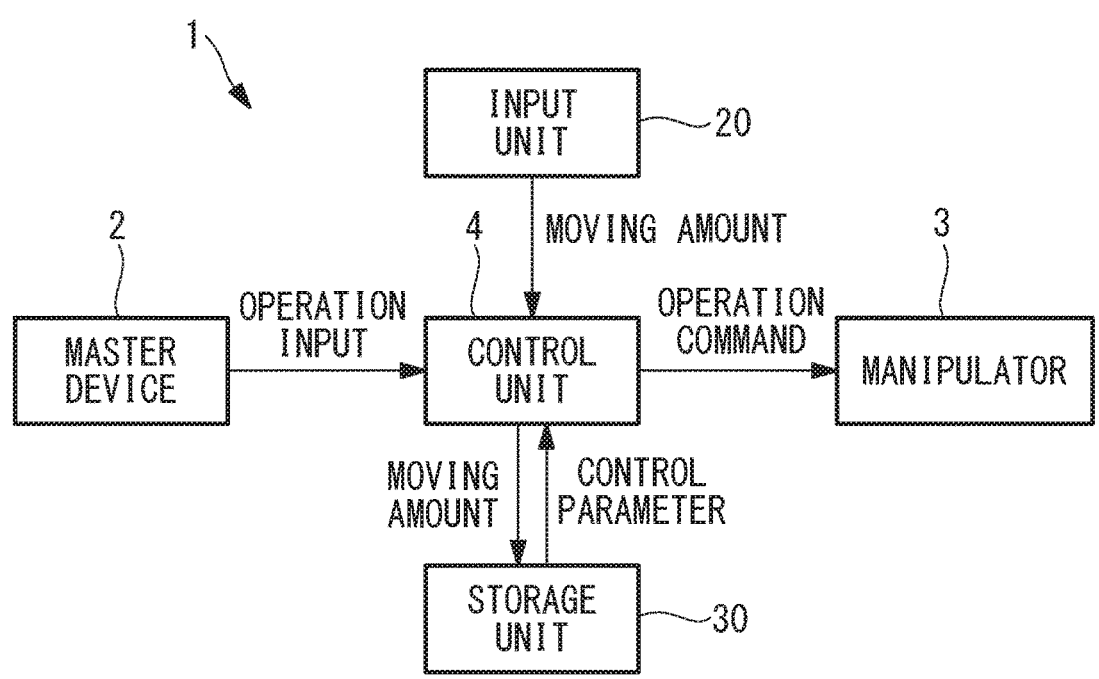
FIG. 4 is a block diagram showing the manipulator system in FIG. 1.

As shown in FIGS. 1 and 4, the manipulator system 1 according to this embodiment is provided with: a master device (operation unit) 2 that is operated by an operator A; a manipulator 3 that is inserted into a body cavity of a patient P; a control unit 4 that controls the manipulator 3 on the basis of an operation input to the master device 2; an input unit (moving-amount input unit) 20; and a storage unit 30. In the figure, reference sign 5 indicates a monitor that displays an endoscope image or the like.

Figure 2A:
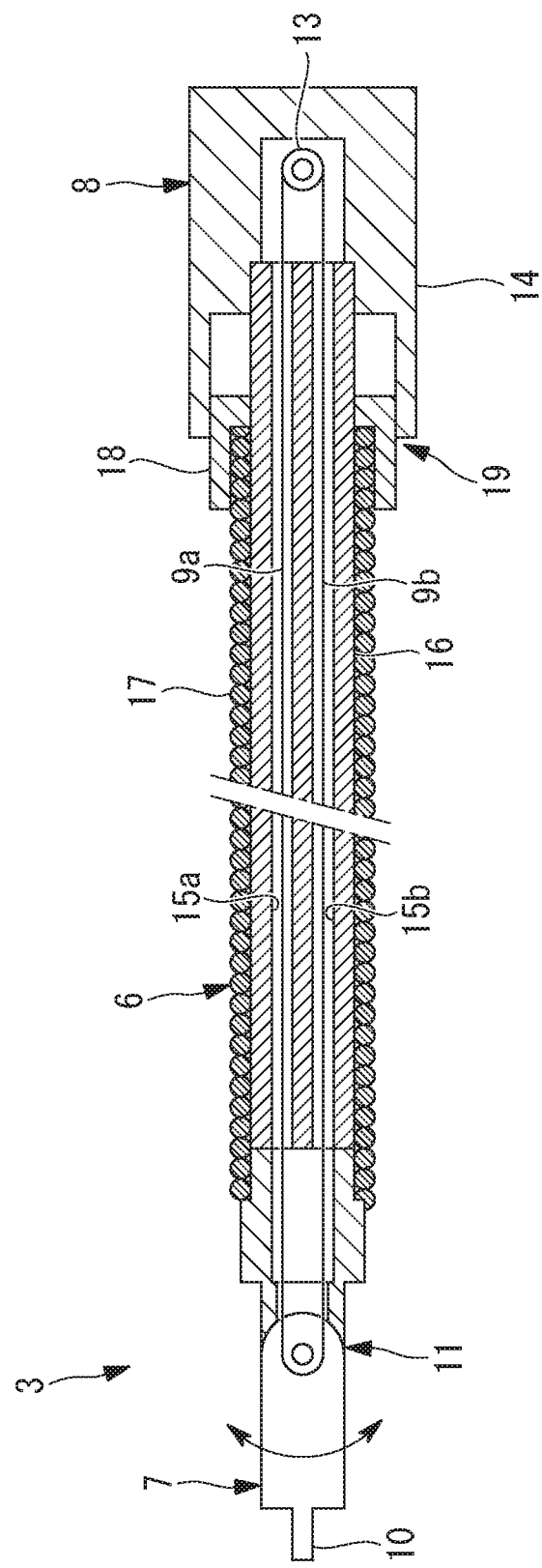
FIG. 2A is a longitudinal cross-sectional view showing a state in which an elongated guide member of a manipulator provided in the manipulator system in FIG. 1 is linearly extended.

As shown in FIGS. 2A and 2B, the manipulator 3 is provided with, for example: a flexible elongated guide member 6 that is inserted into the body cavity of the patient P via a channel of an endoscope 12 inserted into the body cavity of the patient P; a movable portion 7 that is disposed at a distal end of the elongated guide member 6; a drive unit 8 that is disposed at a proximal end of the elongated guide member 6 and that actuates the movable portion 7 by being controlled by the control unit 4; and wires (power transmission members) 9a, 9b that transmit, to the movable portion 7, a driving force generated by the drive unit 8.

The movable portion 7 is provided with: a treatment portion 10, such as forceps, that acts on an affected portion inside the body; and at least one joint portion 11 that supports the treatment portion 10. In an example shown in the figure, in order to simplify the explanation, the joint portion 11 is exemplified as a single pivoting joint that makes the treatment portion 10 pivot about an axis orthogonal to a longitudinal axis of the elongated guide member 6.

The drive unit 8 is provided with: a pulley 13 that is connected to a motor (not shown) that generates a driving force; and a housing 14 that rotatably supports the pulley 13. The two wires 9a, 9b are wound around the pulley 13, and when the pulley 13 is rotated by activation of the motor, a tensile force acts on one of the wires 9a, 9b wound around the pulley 13 depending on the rotation direction of the pulley 13, and the joint portion 11 is driven in one direction by means of the tensile force transmitted by the wire 9a, 9b.

In this embodiment, the elongated guide member 6 is provided with: a multilumen tube (guide tube) 16 having two lumens 15a, 15b through which the two wires 9a, 9b penetrate; a coil tube (outer sheath) 17 that is disposed so as to cover an outer circumferential surface of the multilumen tube 16; and a slider 18 that is fixed to a proximal end of the coil tube 17.

The multilumen tube 16 is formed of a flexible resin material that is easily deformed and has low rigidity. On the other hand, the coil tube 17 is formed of a metal material having higher rigidity than the multilumen tube 16. As shown in FIG. 2A, the coil tube 17 is a tightly wound coil in which strands thereof are in close contact with each other without gaps therebetween in a state in which the elongated guide member 6 is linearly extended.

A distal end of the multilumen tube 16 is fixed to the joint portion 11 and a proximal end of the multilumen tube 16 is fixed to the housing 14 of the drive unit 8. In addition, a distal end of the coil tube 17 is also fixed to the joint portion 11.

The slider 18 is provided so as to be movable with respect to the housing 14 of the drive unit 8 in a longitudinal direction of the multilumen tube 16. By doing so, the proximal end of the coil tube 17 is supported so as to be movable in the longitudinal direction of the multilumen tube 16. In other words, the housing 14 of the drive unit 8 and the slider 18 constitute a guiding mechanism 19 that supports the proximal end of the coil tube 17 so as to be movable in the longitudinal direction of the multilumen tube 16.

As shown in FIG. 2A, in the state in which the elongated guide member 6 is linearly extended, a space is formed between the slider 18 and the housing 14 of the drive unit 8 in the longitudinal direction of the multilumen tube 16.

Figure 3:
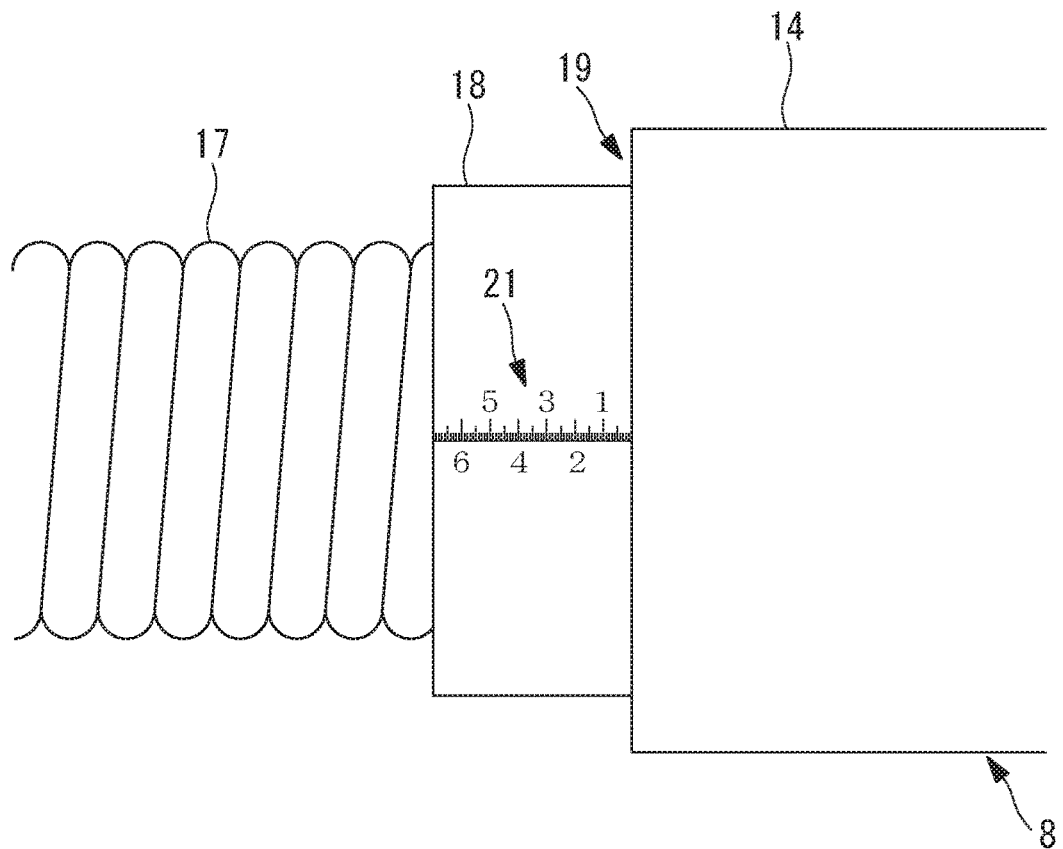
FIG. 3 is a partially enlarged side view showing a moving-amount display portion provided on the manipulator of the manipulator system in FIG. 1.

In addition, in this embodiment, a scale (moving-amount display portion) 21 is provided on the slider 18, as shown in FIG. 3. When the slider 18 moves, the slider 18 becomes accommodated in the housing 14, thereby gradually hiding the scale 21 provided on the slider 18. Therefore, by reading the scale 21 at a position coincident with an end face of the housing 14, it is possible to obtain a moving amount of the slider 18.

The input unit 20 is a device with which the operator who has read the scale 21 inputs the obtained moving amount, and an arbitrary input device, such as a mouse and a keyboard, may be employed.

The storage unit 30 stores a moving amount and a control parameter in association with each other. The control parameter is a coefficient for calculating, with respect to an operation input made using the master device 2, a driving force generated by the drive unit 8 of the manipulator 3.

Here, the relationship between the moving amount of the slider 18 and the shape of the elongated guide member 6 will be described.

As shown in FIGS. 2A and 2B, when the elongated guide member 6 is bent, the highly flexible multilumen tube 16 disposed along the center thereof is bent. Because the multilumen tube 16 is fixed to the movable portion 7 and the drive unit 8 at opposite ends thereof, if the multilumen tube 16 is bent without extending/contracting the length along the center line thereof, the lumens 15a, 15b formed in the multilumen tube 16 do not significantly extend/contract, and thus, the path lengths of the wires 9a, 9b disposed in the lumens 15a, 15b do not significantly vary.

When the multilumen tube 16 is bent, the coil tube 17 covering the outer circumference thereof is also bent. Because the coil tube 17 is formed of a material having sufficiently high rigidity relative to the multilumen tube 16, when the elongated guide member 6 is bent, the coil tube 17 is bent in such a manner that the length of a portion disposed on the inner diameter side of the curve does not change, with the strands thereof being kept in close contact with each other, and that gaps between the strands of a portion disposed on the outer diameter side of the curve are expanded.

With the manipulator 3 according to this embodiment, as shown in FIGS. 2A and 2B, the proximal end of the coil tube 17 is fixed to the slider 18 which is movable with respect to the housing 14 of the drive unit 8 in the longitudinal direction of the multilumen tube 16. Therefore, when the elongated guide member 6 is bent, the slider 18 moves with respect to the housing 14, thereby moving the proximal end of the coil tube 17 to the drive unit 8 side.

In other words, although the length of the coil tube 17 in the portion disposed on the inner diameter side of the curve does not vary between before and after bending, because the proximal end of the coil tube 17 is not fixed, the proximal end of the coil tube 17 is displaced, thus decreasing the space between the slider 18 and the housing 14.

Figure 5:
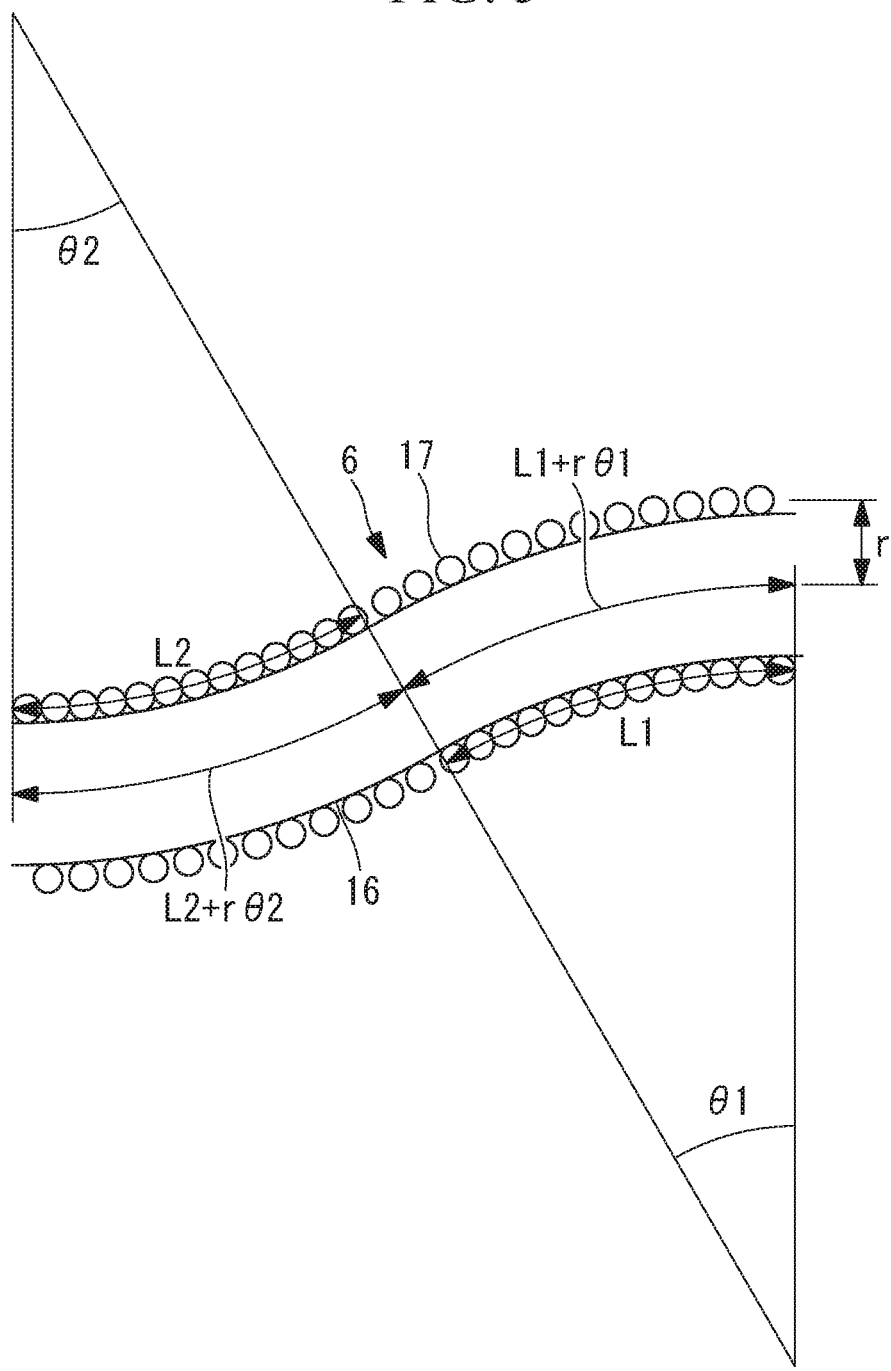
FIG. 5 is a diagram for explaining a moving amount between before and after bending of the elongated guide member of the manipulator of the manipulator system in FIG. 1.

In addition, as shown in FIG. 5, a case in which bending in two directions has occurred in the elongated guide member 6 will be described.

Because the size of the coil tube 17 on the inner diameter side of the curve does not change between before and after bending, the lengths in a first curved portion and a second curved portion are respectively defined as lengths L1 and L2, and the angles in the first curved portion and the second curved portion are respectively defined as angles $\theta 1$ and $\theta 2$.

In addition, assuming that the radius from a center axis of the elongated guide member 6 to center positions of the strands constituting the coil tube 17 is defined as a radius r, the lengths along the center axis of the elongated guide member 6 in the first curved portion and the second curved portion are respectively defined as lengths L1+rθ1 and L2+rθ2.

In other words, the coil tube 17 is extended by $$(L1+r\theta1+L2+r\theta2)-(L1+L2)=r(\theta1+\theta2)$$

between before and after bending, and this extension is the moving amount of the slider 18. That is, the moving amount of the slider 18 is a value obtained by multiplying the total bending angle of the elongated guide member 6 by the radius r. Because the radius r is a constant, it is possible to obtain the total bending angle of the elongated guide member 6 from the moving amount of the slider 18.

This is not limited to the case in which there are two curved portions, and can be applied to a case with an arbitrary number of multiple curved portions.

In other words, the total bending angle $\theta_{flex}$ is expressed by Formula 1.

$$\vartheta_{flex} = \sum_{k=1}^{n} |\vartheta_k| \quad \{\text{Formula 1}\}$$

In addition, by using this total bending angle $\theta_{flex}$, it is possible to calculate a friction force Ff applied to the wire 9a, 9b by $$Ff=Fp\times(1-\exp(-1\times\mu\theta_{flex})).$$

Here, Fp is a tensile force applied to the wire 9a, 9b.

In other words, it is possible to calculate the friction force applied to the wire 9a, 9b by using only the total bending angle $\theta_{flex}$ regardless of the radius of curvature, the bending direction, and the bending angle of each curved portion of the elongated guide member 6. Therefore, it is possible to uniquely obtain, from the moving amount of the slider 18, a control parameter for appropriately controlling the movable portion 7.

The case in which a treatment inside the body of a patient P is performed by using the thus-configured manipulator system 1 according to this embodiment will now be described.

In order to treat an affected portion inside the body by using the manipulator system 1 in FIG. 1, the manipulator 3 according to this embodiment is inserted from the movable portion 7 side at the distal end thereof via the channel of the insertion portion of the endoscope 12 inserted into the body cavity from outside the body of the patient P, and the movable portion 7 is made to protrude from an opening of a forceps channel on a distal end surface of the insertion portion of the endoscope 12 disposed inside the body.

In this case, the body cavity is often winding, and the insertion portion of the endoscope 12 and the channel provided in the insertion portion are inserted into the body cavity by being bent in conformity with the shape of the body cavity. Therefore, in the case in which the manipulator 3 is inserted via such a channel, the manipulator 3 is inserted while bending the elongated guide member 6 in conformity with the channel.

In the manipulator 3 according to this embodiment, when the elongated guide member 6 is bent, the slider 18 moves with respect to the housing 14, thereby moving the proximal end of the coil tube 17 to the drive unit 8 side. In other words, although the length of the coil tube 17 in the portion disposed on the inner diameter side of the curve does not vary between before and after bending, because the proximal end of the coil tube 17 is not fixed, the proximal end of the coil tube 17 is displaced, thus decreasing the space between the slider 18 and the housing 14. As a result, an increase in the tensile force of the multilumen tube 16 is prevented, the length of the multilumen tube 16 is maintained, and an increase in the path length of the wire 9a, 9b is prevented.

In other words, because the path length of the wire 9a, 9b does not vary even when the elongated guide member 6 is bent, it is possible to control the movable portion 7 in a precise manner by preventing the movable portion 7 from being actuated regardless of activation of the drive unit 8 or preventing the wire 9a, 9b from being subjected to an excessive tensile force.

In addition, when the operator obtains the moving amount of the slider 18 by means of the scale 21 and inputs the moving amount via the input unit 20, the control unit 4 reads out the control parameter stored, in association with the moving amount, in the storage unit 30 and controls the manipulator 3 by using the read-out control parameter.

In other words, in the case in which the elongated guide member 6 is bent in a complex manner, the total bending angle $\theta_{flex}$ increases, and thus, friction between the inner walls of the lumens 15a, 15b of the multilumen tube 16 and the wires 9a, 9b increases. Therefore, in order to operate the movable portion 7 against the increased friction force, the control 4 needs to cause the drive unit 8 to generate a larger driving force.

With the manipulator system 1 according to this embodiment, there is an advantage in that it is possible to calculate the total bending angle $\theta_{flex}$ of the elongated guide member 6 by using the moving amount of the slider 18, and that, because the control parameter is changed on the basis of the total bending angle $\theta_{flex}$, even when the friction force applied to the wire 9a, 9b increases, it is possible to cause the drive unit 8 to generate an appropriate driving force, thereby allowing smooth operation of the movable portion 7.

Note that, in this embodiment, as shown in FIGS. 6A to 7B, a locking mechanism 27 that locks the relative positions of the slider 18 and the housing 14 in a state in which the slider 18 is moved, due to bending of the elongated guide member 6, in a direction in which the slider 18 approaches the housing 14 may be provided. In other words, the manipulator 3 of this embodiment is inserted into the channel of the endoscope 12 which is bent by being inserted into a body cavity, and the elongated guide member 6 is bent in conformity with the shape of the channel; however, the shape of the elongated guide member 6 does not significantly change after the insertion is completed.

Therefore, by activation of the locking mechanism 27, the relative positions of the slider 18 and the housing 14 are locked in a state in which the slider 18 is in proximity to the housing 14, and thereby it is possible to make the coil tube 17 receive the compression force applied to the multilumen tube 16.

Figure 7A:
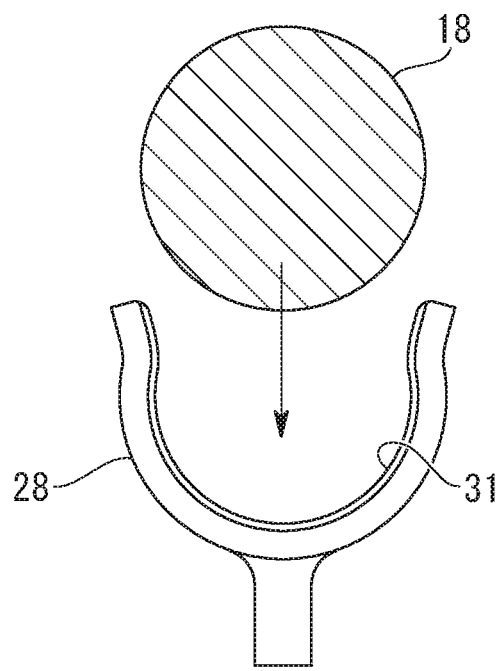
FIG. 7A is a front view for explaining the locking mechanism in FIG. 6A.
Figure 7B:
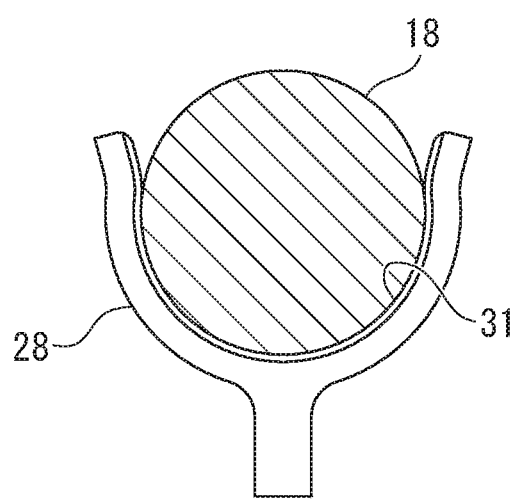
FIG. 7B is a front view for explaining the locking mechanism in FIG. 6B.

As the locking mechanism 27, as shown in FIGS. 7A and 7B, a gripping member 28 that has a substantially C-shaped cross section and that accommodates the slider 18 so as to cover an outer circumferential surface of the slider 18 over substantially half the circumference thereof by being brought into proximity from radially outward of the cylindrical slider 18 may be employed.

Figure 6A:
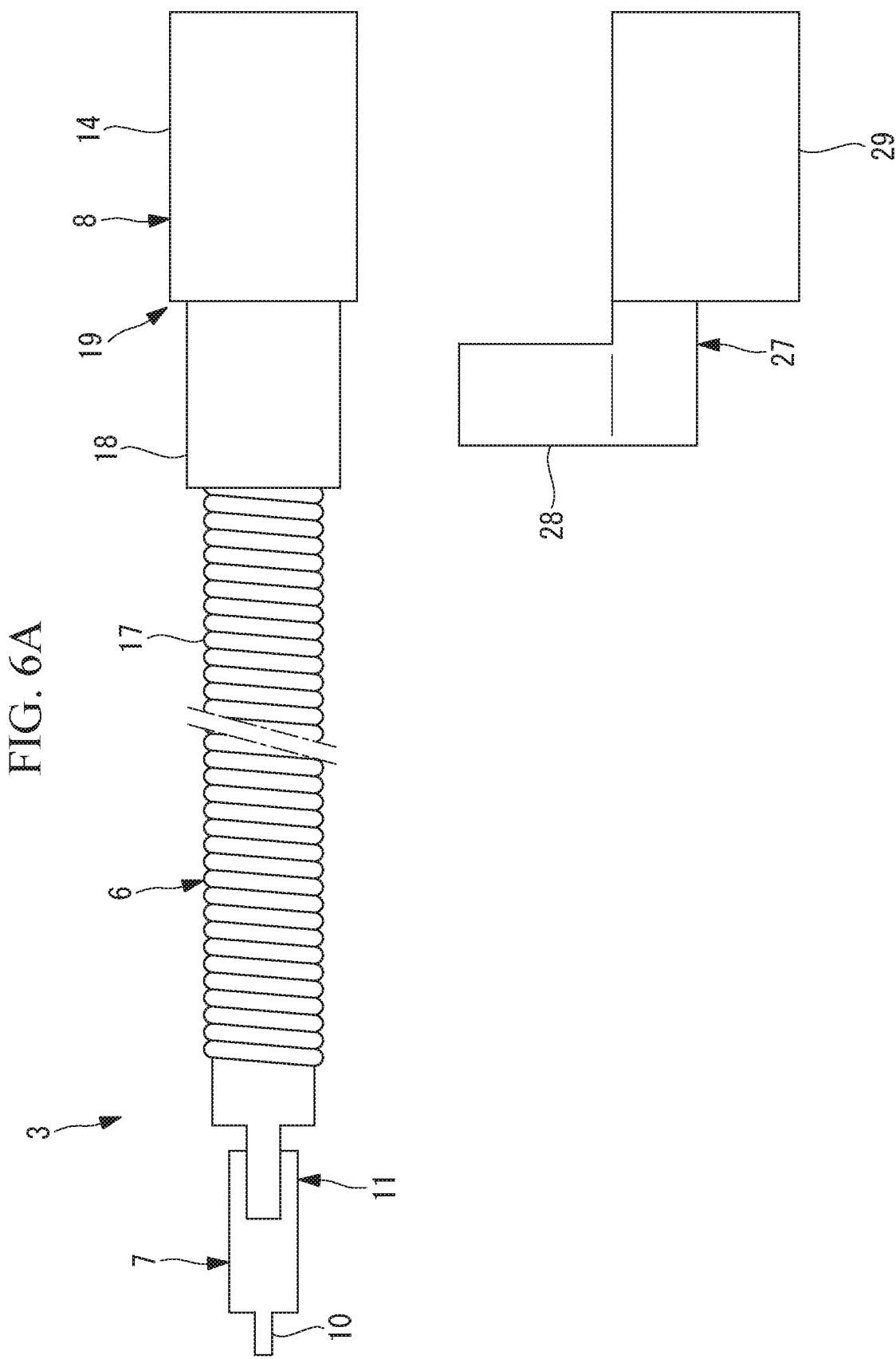
FIG. 6A is a side view showing, as a modification of the manipulator in FIG. 2A, a manipulator provided with a locking mechanism and showing an unlocked state thereof.
Figure 6B:
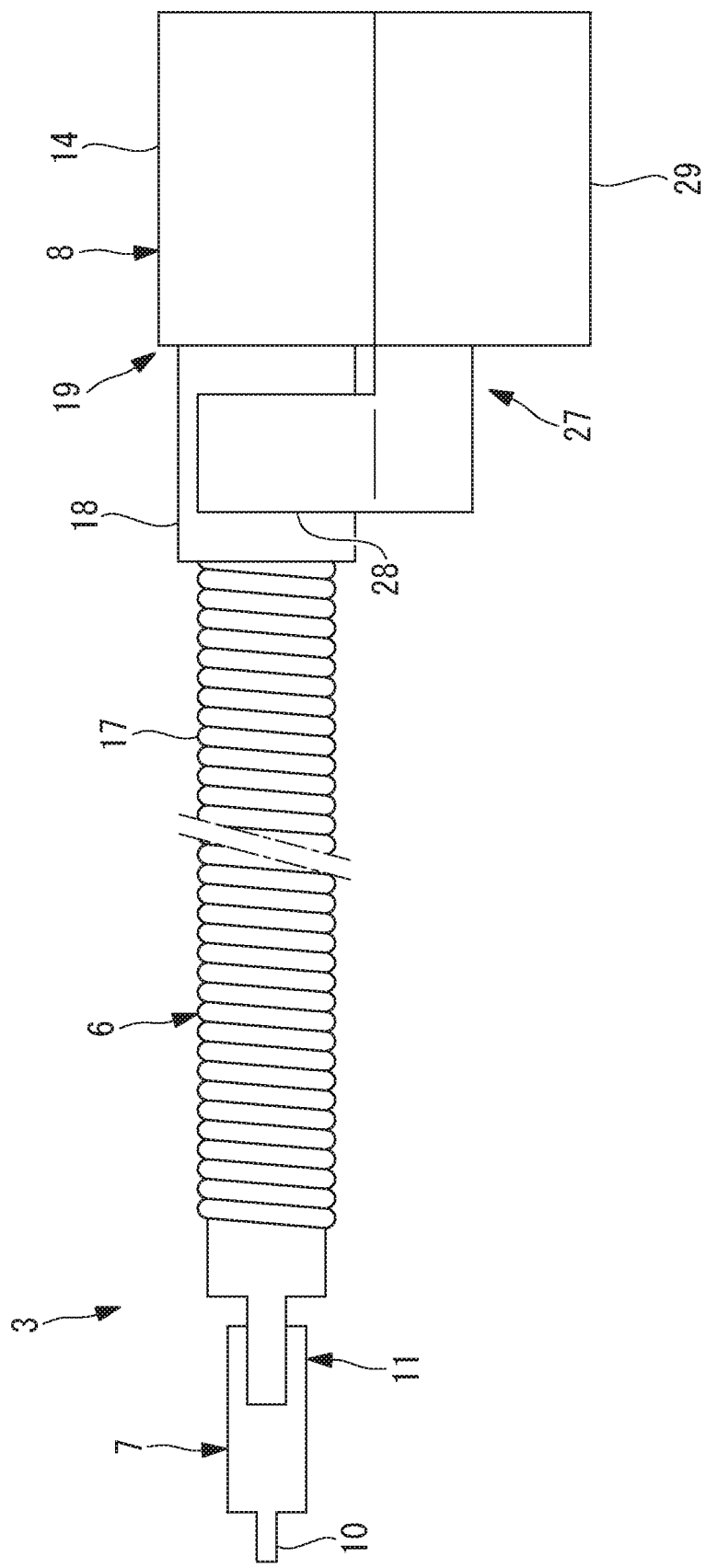
FIG. 6B is a side view showing a locked state of the manipulator in FIG. 6A.

A motor unit 29 that supplies motive power to the drive unit 8 may be provided separately from the drive unit 8 in an attachable/detachable manner. By fixing the gripping member 28 to the motor unit 29, as shown in FIGS. 6B and 7B, the slider 18 is gripped by the gripping member 28 when the drive unit 8 is attached to the motor unit 29, and the structure may be such that the movement of the slider 18 along the longitudinal direction of the multilumen tube 16 is constrained by means of friction between the outer circumferential surface of the slider 18 and the inner circumferential surface of the gripping member 28. In the figures, reference sign 31 indicates a coating formed of a material that increases friction.

In addition, although the moving amount of the slider 18 is obtained by means of the scale 21 and input via the input unit 20 in this embodiment, alternatively, as shown in FIG. 8, a sensor (moving-amount detection unit) 32 that detects the moving amount of the slider 18 may be provided.

Figure 9A:
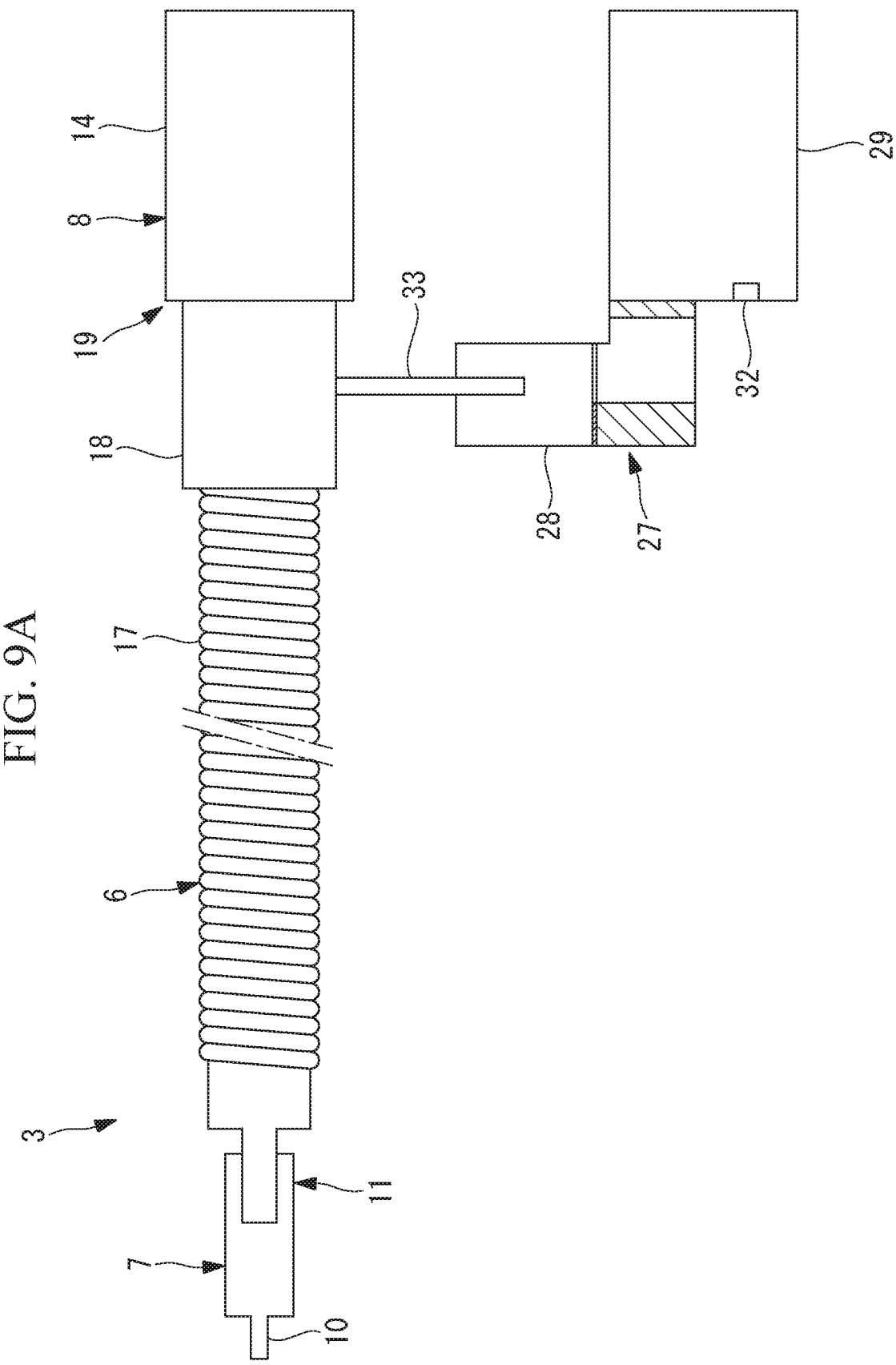
FIG. 9A is a diagram showing an example of a sensor provided in the manipulator system in FIG. 8.
Figure 9B:
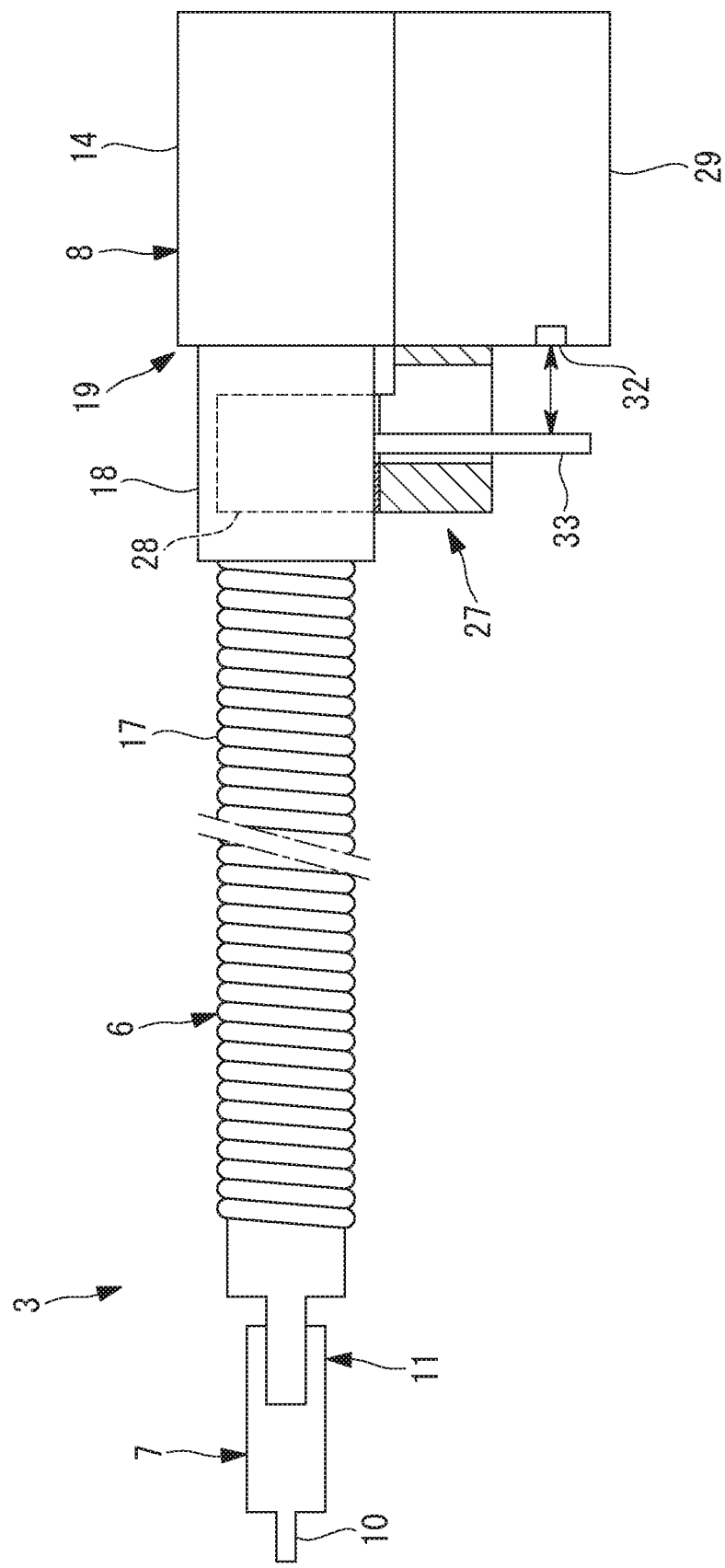
FIG. 9B is a side view showing a locked state of the manipulator in FIG. 9A.

As the sensor 32, as shown in FIGS. 9A and 9B, a range finding sensor that directly detects the moving amount of a plate 33 fixed to the slider 18 may be employed. By doing so, it is possible to separate a disposable portion and a reusable portion, and to provide the range finding sensor on the motor unit 29, which is the reusable portion. In addition, a pulley (not shown) that is linked to the movement of the slider 18 may be provided, and an encoder (not shown) that indirectly detects the moving amount of the slider 18 by detecting a rotation angle of the pulley may be employed.

Figure 10A:
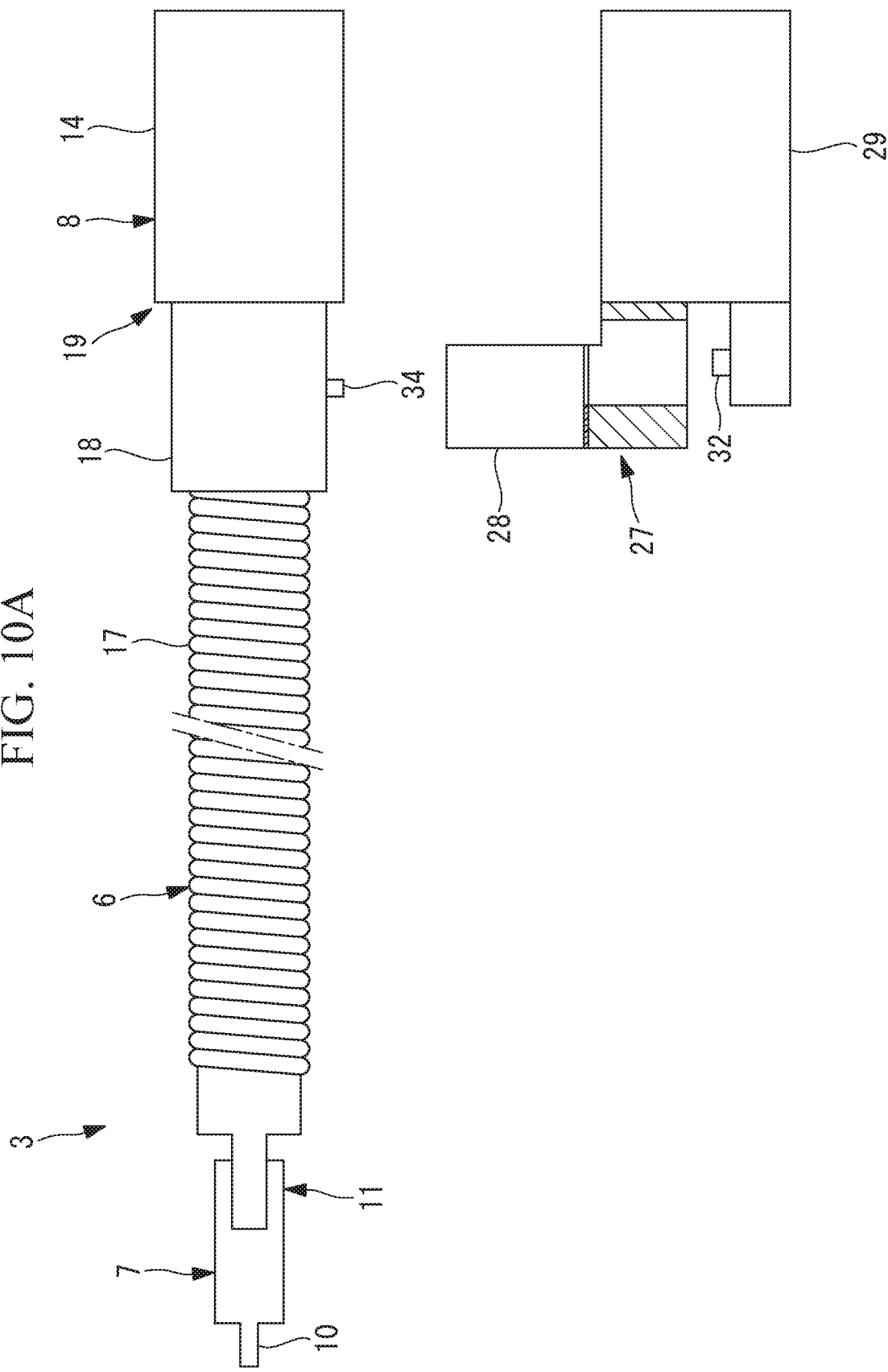
FIG. 10A is a diagram showing another example of the sensor provided in the manipulator system in FIG. 8.
Figure 10B:
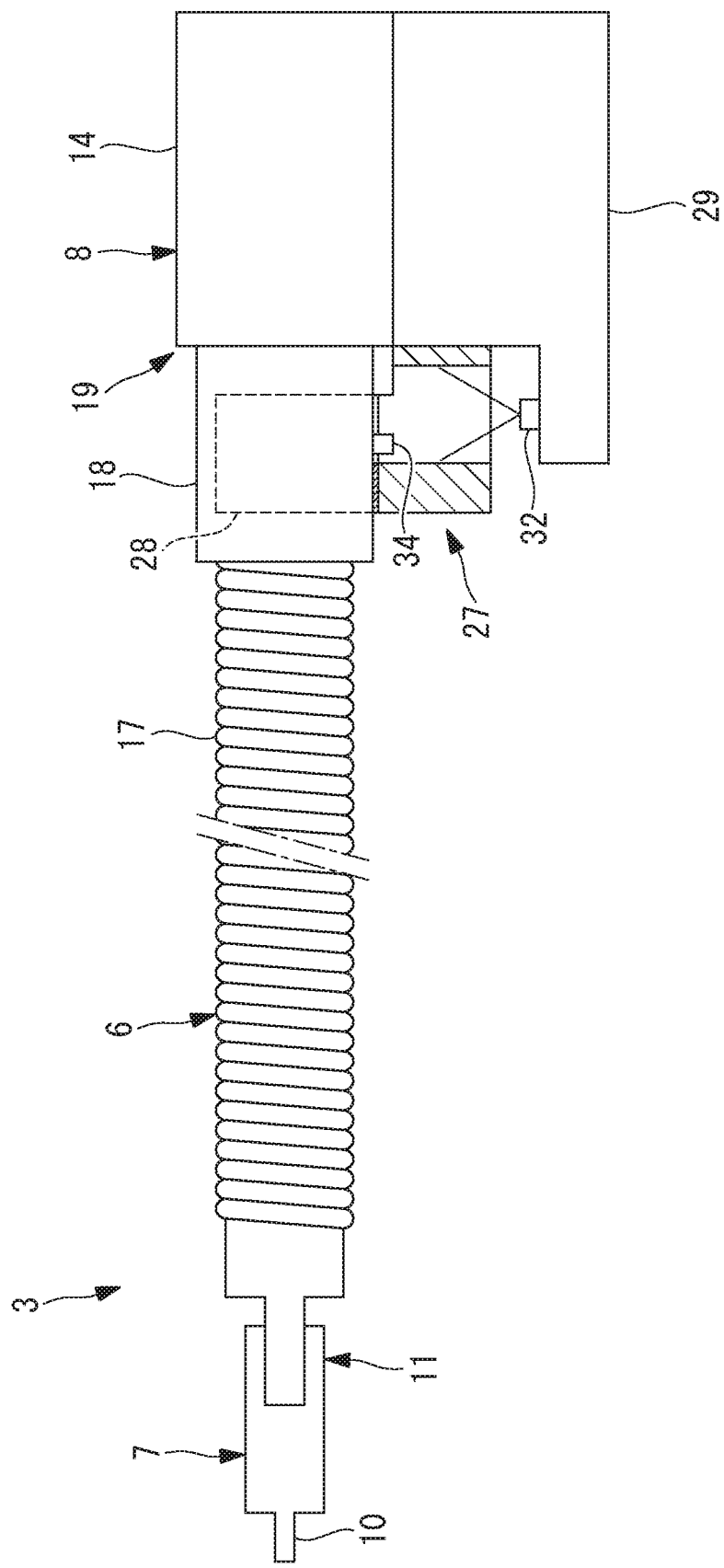
FIG. 10B is a side view showing a locked state of the manipulator in FIG. 10A.

In addition, as shown in FIGS. 10A and 10B, a camera that acquires an image of the slider 18 may be employed as the sensor 32, and, for example, the moving amount of the slider 18 may be detected by detecting the position of a marker 34 provided on the slider 18 by means of image processing.

By employing the sensor 32, it is possible to input the moving amount of the slider 18, which is detected by the sensor 32, directly to the control unit 4, and to eliminate the input operation by the operator.

Figure 11:
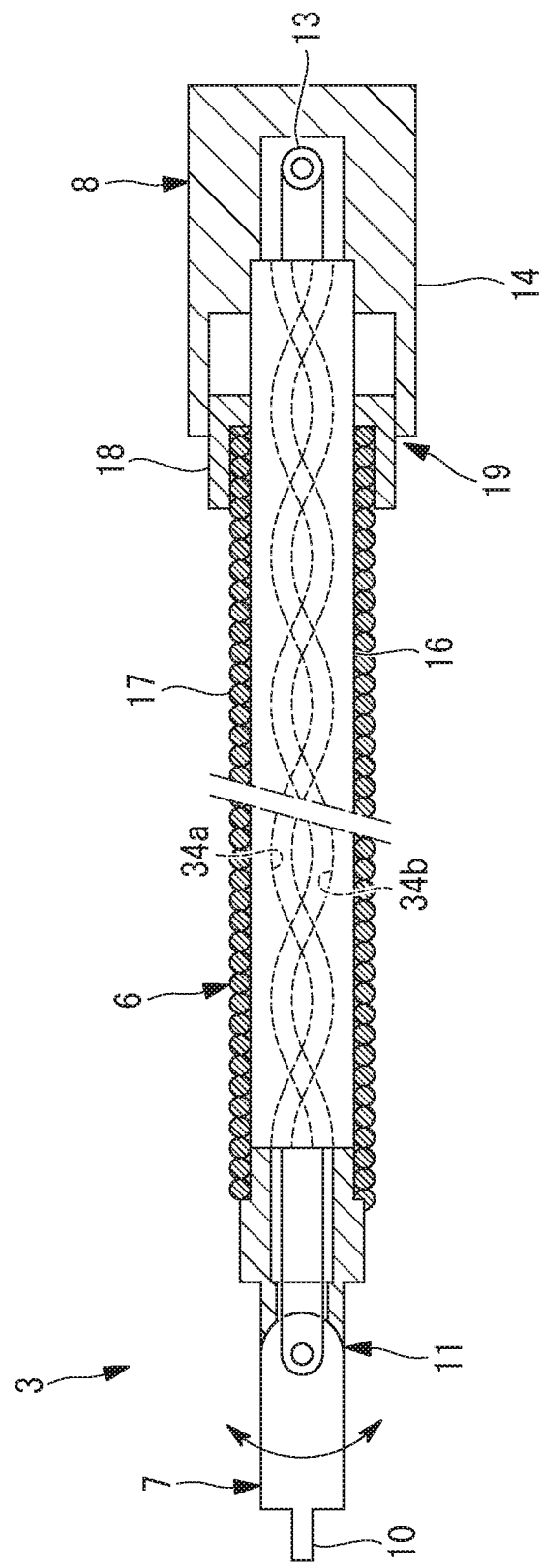
FIG. 11 is a partial longitudinal cross-sectional view showing a modification of the manipulator in FIG. 2A in which a multilumen tube having a twisted lumen is provided as a guide tube.

In addition, in this embodiment, the multilumen tube 16 in which the plurality of lumens 15a, 15b are formed in a straight line along the longitudinal direction of the multilumen tube 16 has been illustrated as an example. However, this embodiment is not limited thereto, and, as shown in FIG. 11, a multilumen tube 16 having lumens 34a, 34b that are twisted about the longitudinal axis of the multilumen tube 16 may be employed.

By doing so, by using the thick multilumen tube 16, it is possible to suppress variations in the length of each of the lumens 34a, 34b due to bending even if a difference in the radius of curvature becomes large during bending, and thus, it is possible to prevent variations in the path length of the wire 9a, 9b.

Figure 12:
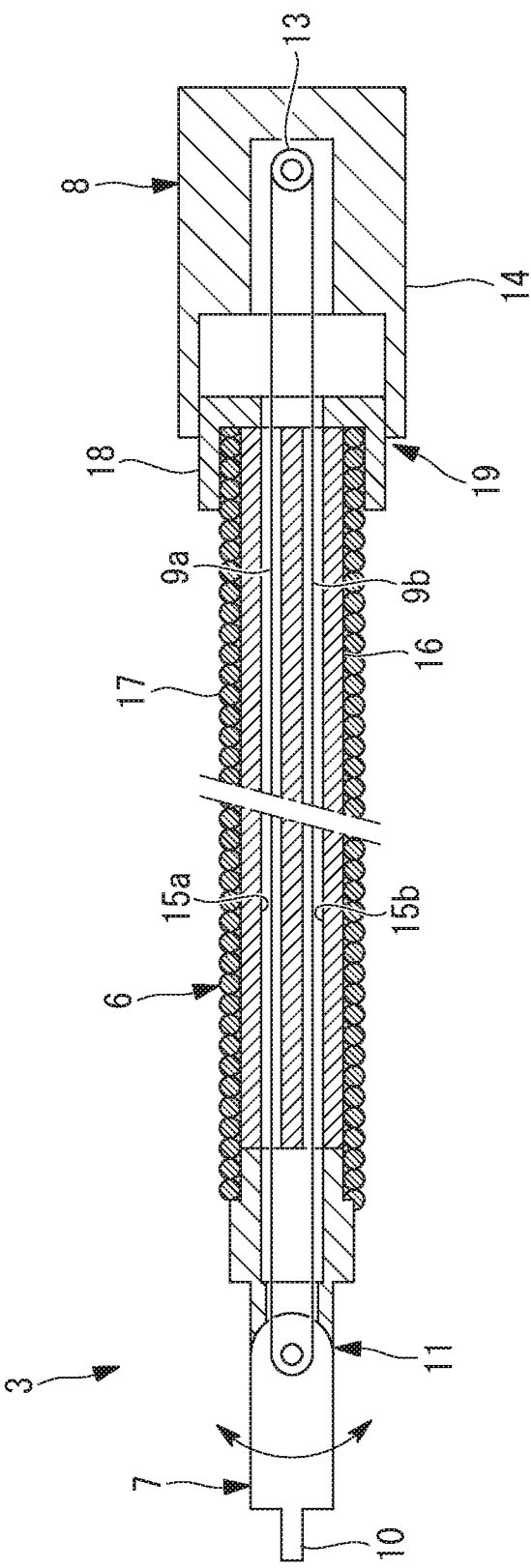
FIG. 12 is a partial longitudinal cross-sectional view showing a modification of the manipulator in FIG. 2A in which a proximal end of the guide tube is connected to a proximal end of an outer sheath.

In addition, although the proximal end of the multilumen tube 16 is fixed to the housing 14 in the manipulator 3 of this embodiment, alternatively, as shown in FIG. 12, a manipulator in which the proximal end of the multilumen tube 16 is fixed to the proximal end of the coil tube 17 may be used.

By doing so, the proximal end of the multilumen tube 16 is attached so as to be movable with respect to the housing 14 of the drive unit 8 in the longitudinal direction of the elongated guide member 6. In this case, by moving the elongated guide member 6 with respect to the drive unit 8 in the longitudinal direction of the multilumen tube 16, it is possible to compensate for the compression amount of the innermost diameter portion with the moving amount of the slider 18 fixed to the proximal end of the coil tube 17. In addition, it is possible to stably transmit the driving force by suppressing extension of the multilumen tube 16 caused by friction with the wire 9a, 9b passing through the interior thereof. In other words, it is possible to bend the elongated guide member 6 while suppressing unstable power transmission due to wire driving.

In addition, although the guide tube 16 has been illustrated in the form of a multilumen tube in the manipulator 3 of this embodiment, alternatively, a guide tube 16 constituted of a plurality of coil tubes 17 may be used.

As a result, the above-described embodiment also leads to the following aspect.

An aspect of the present invention is directed to a manipulator system comprising: a manipulator; an operation unit for performing an input for operating the manipulator; and a control unit that controls the manipulator on the basis of the input to the operation unit, wherein the manipulator comprises a movable portion, a drive unit that generates motive power to be supplied to the movable portion, a flexible elongated guide member to which the movable portion is attached at one end thereof and the drive unit is attached at the other end thereof, and a power transmission member that transmits the motive power of the drive unit to the movable portion, wherein the elongated guide member comprises a flexible guide tube that has a lumen through which the power transmission member penetrates in a longitudinal direction thereof, and an outer sheath that covers an outer circumference of the guide tube and that has higher rigidity than the guide tube, wherein a proximal end of the outer sheath is attached so as to be movable with respect to the drive unit in the longitudinal direction of the elongated guide member, and wherein the control unit changes a control parameter in accordance with a moving amount of the outer sheath.

With this aspect, when an operator performs an input by operating the operation unit, the control unit controls the manipulator on the basis of the input to the operation unit, thereby activating the manipulator. In the manipulator, motive power generated at the drive unit due to activation of the drive unit is transmitted to the movable portion via the power transmission member, thereby activating the movable portion.

When the elongated guide member is bent, the guide tube and the outer sheath constituting the elongated guide member are bent and the lumen provided in the guide tube is also bent, and thus, the power transmission member is guided in the bent lumen so as to transmit the motive power. In addition, with the outer sheath having higher rigidity than the guide tube, it is possible to transmit, to the movable portion, a torque about a longitudinal axis being applied by the drive unit.

In this case, when the elongated guide member is bent by a large amount, the length dimension of a portion of the high-rigidity outer sheath, said portion being disposed in an innermost diameter portion on the innermost side of the curve, does not change. Because of this, in the case in which opposite ends of the outer sheath are fixed to the movable portion and a fixed portion, the dimension of the elongated guide member after bending is determined on the basis of the innermost diameter portion; thus, the guide tube which is disposed more radially outward of the curve than the innermost diameter portion is extended on the basis of a difference in a radius of curvature, which also causes the lumen length to be extended and increases the path length of the power transmission member.

With this aspect, by moving the proximal end of the outer sheath with respect to the drive unit in the longitudinal direction of the guide tube between before and after bending of the elongated guide member, it is possible to compensate for the compression amount of the innermost diameter portion with the moving amount of the outer sheath, and to suppress variations in the path length of the power transmission member by suppressing extension of the guide tube. By doing so, it is possible to bend the elongated guide member while preventing excessive variations in the tensile force on the power transmission member due to variations in the path length thereof.

In this case, the moving amount of the proximal end of the outer sheath with respect to the drive unit is proportional to the total bending angle of the elongated guide member. In addition, a friction force between the lumen and the power transmission member that is brought into contact with the inner wall of the lumen is determined on the basis of the total bending angle of the elongated guide member. Therefore, by changing the control parameter in accordance with the moving amount of the outer sheath, it is possible to appropriately perform control of the manipulator in consideration of the friction force between the lumen and the power transmission member.

In the abovementioned aspect, a proximal end of the guide tube may be attached so as to be movable with respect to the drive unit in the longitudinal direction of the elongated guide member.

By doing so, in the case in which the proximal end of the outer sheath and the proximal end of the guide tube are fixed, by moving the elongated guide member with respect to the drive unit in the longitudinal direction of the guide tube, it is possible to compensate for the compression amount of the innermost diameter portion with the moving amount of the outer sheath, and to stably transmit the driving force by suppressing extension of the guide tube caused by friction with the wire passing through the interior thereof. By doing so, it is possible to bend the elongated guide member while suppressing unstable power transmission due to wire driving.

In the abovementioned aspect, a moving-amount display portion that displays the moving amount of the outer sheath and a moving-amount input unit that inputs the moving amount of the outer sheath may be provided, and the control unit may change the control parameter in accordance with the moving amount input from the moving-amount input unit.

By doing so, when the elongated guide member is bent, the proximal end of the outer sheath is moved with respect to the drive unit, and the moving amount thereof is displayed by the moving-amount display portion. When the operator inputs the moving amount displayed on the moving-amount display portion to the moving-amount input unit, the control unit changes the control parameter in accordance with the input moving amount, and thereby it is possible to appropriately perform control of the manipulator in consideration of the friction force between the lumen and the power transmission member.

In addition, in the abovementioned aspect, a moving-amount detection unit that detects the moving amount of the outer sheath may be provided, and the control unit may change the control parameter in accordance with the moving amount detected by the moving-amount detection unit.

By doing so, when the elongated guide member is bent, the proximal end of the outer sheath is moved with respect to the drive unit, and the moving amount thereof is detected by the moving-amount detection unit. Then, the control unit changes the control parameter in accordance with the detected moving amount, and thereby it is possible to appropriately perform control of the manipulator in consideration of the friction force between the lumen and the power transmission member.

In addition, in the abovementioned aspect, the outer sheath may be provided so as to be movable with respect to the drive unit, and a locking mechanism that fixes the outer sheath and the drive unit at arbitrary relative positions may be provided.

The manipulator is, for example, inserted into a channel of an endoscope which is bent by being inserted into a body cavity, and the elongated guide member is bent in conformity with the shape of the channel of the endoscope; however, the shape of the elongated guide member does not significantly change after the insertion is completed. Because of this, when the elongated guide member is bent, the proximal end of the outer sheath moves in a direction in which the proximal end thereof approaches the drive unit disposed on the proximal end side. After the insertion of the manipulator into the channel of the endoscope is completed, the relative positions of the outer sheath and the drive unit are locked in a state in which the outer sheath is in proximity to the drive unit by activation of the locking mechanism. By doing so, a larger portion of the guide tube is covered with the outer sheath having higher rigidity, and when driving the movable portion by means of the drive unit, it is possible to make the outer sheath receive the compression force applied to the guide tube.

In addition, in the abovementioned aspect, the lumen may have a shape in which the lumen is twisted about a longitudinal axis of the guide tube.

By doing so, when the flexible guide tube is bent, although the shape of the lumen is also changed with the bending thereof, a contact state between the inner surface of the lumen having the shape in which the lumen is twisted about the longitudinal axis of the guide tube and a power transmission member penetrating through the lumen does not significantly change due to the bending state of the insertion portion. As a result, because it is not necessary to make a significant change in the motive power generated by the drive unit in accordance with the bending state, it is possible to enhance the maneuverability or controllability of the movable portion.

The present invention affords an advantage in that it is possible to bend an insertion portion without excessively increasing the tensile force that acts on a power transmission member penetrating through a lumen, and to appropriately operate a movable portion in accordance with a bent form.

REFERENCE SIGNS LIST

1 manipulator system
2 master device (operation unit)
3 manipulator
4 controller
6 elongated guide member
7 movable portion
8 driver
9a, 9b wire (power transmission member)
15a, 15b, 34a, 34b lumen
16 multilumen tube (guide tube)
17 coil tube (outer sheath)
20 input unit (moving-amount input unit)
21 scale (moving-amount display portion)
27 locking mechanism
32 sensor (moving-amount detection unit)

The invention claimed is:
1. A manipulator system comprising:
an actuator provided at a proximal end of an elongated guide member to drive a distal end of the elongated guide member, a slider that is fixed to the proximal end of the elongated guide member and that is configured to move with respect to the actuator in a longitudinal direction of the elongated guide member, and a controller that is configured to control the actuator so as to change a moving amount of the slider in accordance with a bending state of the elongated guide member.

2. The manipulator system according to claim 1, wherein the elongated guide member comprising:

a guide tube that has a lumen through which a wire for transmitting a driving force of the actuator penetrates in the longitudinal direction thereof; and an outer sheath that covers an outer circumference of the guide tube.

3. The manipulator system according to claim 2, wherein a proximal end of the guide tube is attached and configured to move with respect to the actuator in the longitudinal direction of the elongated guide member.

4. The manipulator system according to claim 2, wherein the lumen has a shape in which the lumen is twisted about a longitudinal axis of the guide tube.

5. The manipulator system according to claim 1, wherein the controller is configured to change a control parameter corresponding to a moving amount of the elongated guide member.

6. The manipulator system according to claim 2, wherein the controller is configured to calculate a control parameter that is generated when the elongated guide member is bent and that corresponds to a path length of the elongated guide member, and is configured to control a driving force of the actuator, corresponding to a friction force of the wire, on a basis of the control parameter.

7. A manipulator control method comprising:

detecting, by a sensor, an amount by which a slider, which is connected to a proximal end of an elongated guide member, moves by causing a distal end of the elongated guide member to bend with respect to the proximal end of the elongated guide member; and controlling, by a controller, an actuator so as to change a moving amount of the slider on a basis of a result of detection by the sensor.

* * * * *